United States Patent [19]
Garcia et al.

[11] Patent Number: 5,097,525
[45] Date of Patent: Mar. 17, 1992

[54] OPTICAL TRANSMISSION DEVICE

[75] Inventors: Gerald W. Garcia, Redwood City; Bimal K. Deka; Stuart Harman, both of San Jose, all of Calif.; James A. Harrington, Martinsville, N.J.

[73] Assignee: Heraeus Lasersonics, Inc., Milpitas, Calif.

[21] Appl. No.: 501,651

[22] Filed: Mar. 29, 1990

Related U.S. Application Data

[63] Continuation-in-part of Ser. No. 164,236, Mar. 4, 1988, Pat. No. 4,917,083.

[51] Int. Cl.⁵ .................... G02B 6/36; G02B 7/26
[52] U.S. Cl. .................................................. 385/75
[58] Field of Search ..................... 350/96.2, 96.21

[56] References Cited

U.S. PATENT DOCUMENTS

| | | | |
|---|---|---|---|
| 4,822,129 | 4/1989 | Webb | 350/96.2 |
| 4,904,035 | 2/1990 | Heckmann et al. | 350/96.2 |
| 4,919,505 | 4/1990 | Bartosiak et al. | 350/96.2 |
| 4,919,510 | 4/1990 | Hoke et al. | 350/96.2 |
| 4,925,266 | 5/1990 | Huebscher et al. | 350/96.2 |
| 4,938,558 | 7/1990 | Miller et al. | 350/96.2 |

*Primary Examiner*—William L. Sikes
*Assistant Examiner*—Robert E. Wise
*Attorney, Agent, or Firm*—Townsend and Townsend

[57] ABSTRACT

An optical transmission device comprising a body, a tapered surface disposed in the body, and means for attaching an optical transmission means to the body. In the preferred embodiment, the optical transmission means is a hollow waveguide. The tapered surface has an inlet aperture for receiving radiation and an outlet aperture. The diameter of the outlet aperture of the tapered surface is smaller than the inner diameter of the hollow waveguide.

20 Claims, 2 Drawing Sheets

OPTICAL TRANSMISSION DEVICE

This application is a continuation-in-part of U.S. Pat. application Ser. No. 164,236, filed Mar. 4, 1988, now U.S. Pat. No. 4,917,083.

BACKGROUND OF THE INVENTION

This invention relates generally to an optical transmission device and, in particular, a device for connecting an optical waveguide to a laser light source.

Waveguides are devices that reflectively transmit light along their length. Waveguides may be hollow or solid, and may be formed from stainless steel-jacketed sapphire, ceramic alumina, or other materials known in the art. As discussed in U.S. Pat. application Ser. No. 164,236 (filed Mar. 4, 1988), one particular use of waveguides is to deliver laser light from a source to a patient for surgery. Many other uses of laser waveguides are possible, however, and are known to those skilled in the art.

Prior art waveguides are attached to the laser light source through a connector whose purpose is to align the waveguide with the path of the laser light. One example of the prior art is the OFTI STC connector manufactured by Optical Fiber Technologies, Inc. of Billerica, Mass.

SUMMARY OF THE INVENTION

One shortcoming of prior art waveguide connectors arises when the laser beam directed to the waveguide becomes slightly misaligned. For example, if, instead of entering the core of a hollow waveguide, the laser light strikes the exposed leading edge of the wave guide, the waveguide material could be damaged or destroyed, potentially compromising the performance of the system.

This invention overcomes this problem by providing a waveguide connector that protects the leading edge of the waveguide core from the harmful effects of misdirected laser light. The optical transmission device has a body, a tapered surface disposed in the body, and means for attaching an optical transmission component to the body. In the preferred embodiment, the optical transmission means is a hollow waveguide. The tapered surface has an inlet aperture for receiving radiation and an outlet aperture. The diameter of the outlet aperture of the tapered surface is smaller than the inner diameter of the hollow waveguide. The tapered surface therefore protects the leading edge of the waveguide from the laser radiation. In addition, the tapered surface can reflect misdirected laser radiation into the waveguide.

The preferred embodiment of the invention is described below with reference to the drawings.

DETAILED DESCRIPTION OF THE PREFERRED EMBODIMENT

Figure 1:
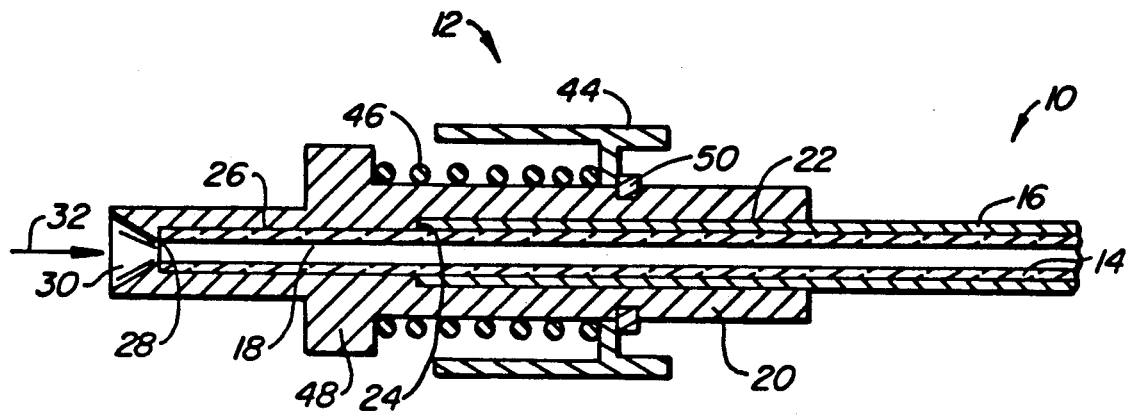
FIG. 1 is a sectional view of the preferred embodiment of this invention.
Figure 2:
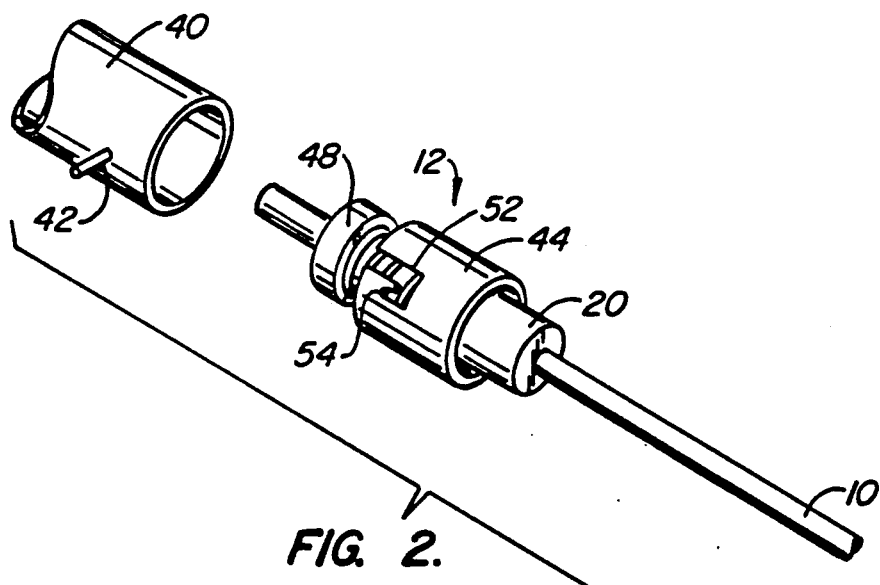
FIG. 2 is an elevational view of the preferred embodiment of this invention.

FIGS. 1 and 2 show the preferred embodiment of this invention. As seen in FIG. 1, a waveguide 10 (partially shown) is mounted in a connector 12. In the preferred embodiment, waveguide 10 consists of a hollow sapphire core 14 and stainless steel jacket 16. It should be understood that other types of waveguides and waveguide materials may be mounted in connector 12 without departing from the invention.

The waveguide extends into a bore 22 formed in the body 20 of connector 12. In the preferred embodiment, body 20 is machined in one piece from stainless steel. A portion 18 of core 14 extends beyond jacket 16 into a smaller diameter bore 26 formed in body 20. The inner end of jacket 16 rests against a shoulder 24 formed at the transition between bore 22 and bore 26. Jacket 16 and the exposed portion 18 of core 14 are preferably bonded to bores 22 and 26, respectively, by an epoxy compound.

The end of portion 18 of core 14 rests against another shoulder 28 remote from shoulder 24. A tapered, conical surface 30 begins at shoulder 28 and extends outward to the leading edge of the connector body 20. Depending upon the characteristics of the laser beam, the included angle of the conical surface 30 may vary between 1° and 85°, although the angle is preferably between 7° and 60°, inclusive. The innermost diameter of conical surface 30 (i.e. the point of surface 30 closest to shoulder 28) must be smaller than the inner diameter of core 14, for the reasons explained below. Bores 22 and 26 and conical surface 30 are preferably formed by machining.

The preferred mechanism for connecting the waveguide to the laser light source is known in the art and will be explained only briefly. As shown in FIG. 2, the laser light source 40 is provided with a pair of oppositely disposed bayonets 42. In the preferred embodiment, source 40 is a coupler at the end of an articulated mirror arm that transmits the laser beam from a remote source, such as that disclosed in U.S. Pat. application Ser. No. 164,236, filed Mar. 4, 1988.

As seen in FIGS. 1 and 2, a bayonet nut 44 surrounds body 20 of connector 12. Bayonet nut 44 is biased to the right (i.e., away from conical surface 30) by spring 46 which rests against a ring 48 projecting from the outer surface of connector body 20. A C-clip 50 disposed in a groove formed in the surface of body 20 limits the rightward travel of nut 44.

A pair of hook-shaped grooves 52 is formed in nut 44, one of which is shown in FIG. 2. To attach connector 12 to the laser source, the leading portion 21 of body 20 is inserted into an aperture 54 in the source until ring 48 abuts the face of the source. Bayonet nut 44 is moved forward against the spring bias with grooves 52 aligned with bayonets 42, then twisted so that bayonets 42 enter notches 54 formed at the end of each groove 52. This action holds the connector tightly against the source.

In operation, laser light enters connector 12 as shown by arrow 32. Conical surface 30 serves three functions. First, if the laser beam is slightly misaligned and strikes surface 3 instead of entering the waveguide aperture, conical surface 30 will redirect the beam into the waveguide. Second, if the laser beam 32 is so misdirected that it will not reflect into the waveguide aperture, conical surface 30 and the rest of the connector body absorb or disperse the beam's energy, thereby protecting the relatively fragile sapphire core.

Finally, keeping the innermost diameter of surface 30 smaller than the inner diameter of sapphire core 14 prevents the laser beam from hitting the annular leading edge of core 14. By protecting the leading edge of the core from off-axis laser energy, this invention will prolong the useful life of the waveguide.

The preferred material for conical surface 30 depends on the laser light used. For $CO_2$ lasers, stainless steel with a smooth, highly polished surface meets both the reflective and heat absorptive requirements of the invention. Invar, nickel, platinum, or any other high specific heat metal or alloy may be substituted for the stainless steel for $CO_2$ laser applications. For light in the visible range, such as HeNe lasers, surface 30 may be formed from stainless steel or any of the other metals mentioned above and coated with gold or other reflective material. A gold coating on conical surface 30 will also enhance the reflection of $CO_2$ laser light.

Figure 3:
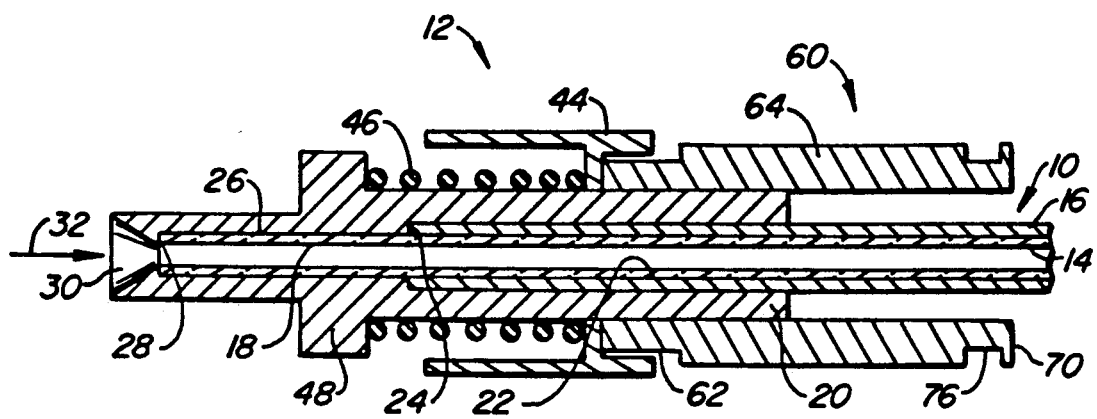
FIG. 3 is a sectional view of the preferred embodiment of this invention with an accessory attachment feature.
Figure 4:
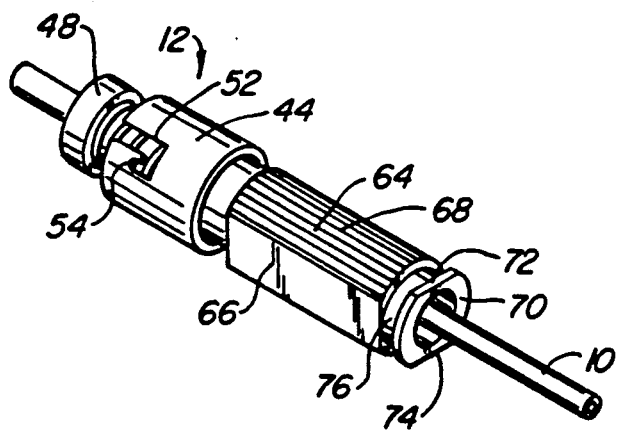
FIG. 4 is an elevational view of the preferred embodiment of this invention with an accessory attachment.

FIGS. 3 and 4 show an alternative embodiment of this invention. In this embodiment, connector 12 is provided with a Luer lock 60 to permit attachment to accessories. Lock 60 has a first narrow portion 62 that is partially surrounded by bayonet nut 44. In this embodiment, nut 44 rests against lock 60 instead of against a C-clip 50 as in the first embodiment.

Lock 60 has a main body portion 64 with a flattened surface 66 and a knurled cylindrical surface 68. A ring 70 with two flattened edges 72 and 74 extends from a second narrow portion 76.

Figure 5:
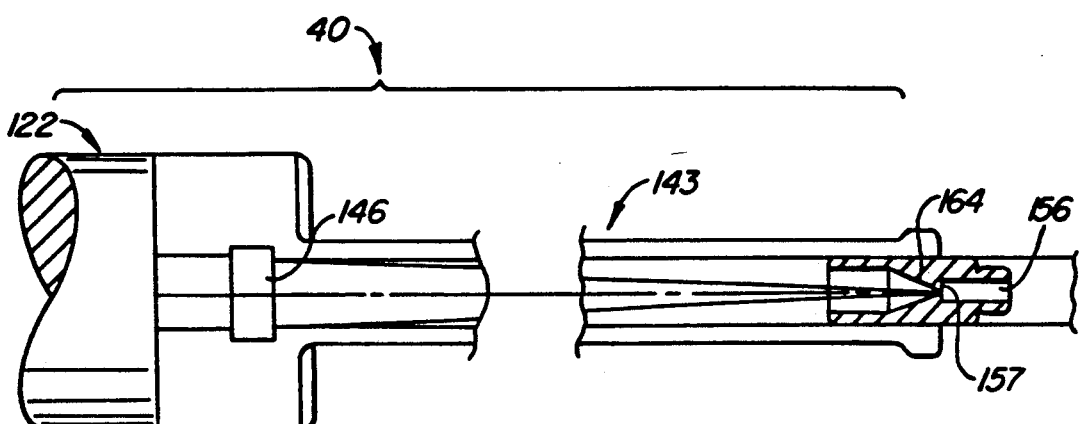
FIG. 5 is a partial sectional view of an alternative embodiment of this invention.

Instead of being located in the connector, the conical surface may be disposed upstream of the connector in the laser light source. With reference FIG. 5, the light source 40 is a coupler 143 mounted on the end of an articulated arm 122. The coupler 143 includes a lens 146 located on its center line to focus the laser radiation into the waveguide aperture. A conical surface 164 is formed upstream of a bore 156 for receiving a waveguide. The diameter of the smaller, downstream aperture of the conical surface is smaller than the diameter of bore 156, thereby forming a shoulder 157 against which the end of the waveguide will rest. As in the previous embodiment, the diameter of the downstream aperture of the conical surface should be smaller than the inner diameter of the hollow waveguide. In addition, conical surface 164 may be coated with a reflective material such as gold in order to operate more effectively in the visible range of light. By placing the tapered surface 164 in the coupler member and not in the waveguide connector, a standard waveguide connector may be used, if desired.

Modifications may be made to this device without departing from the scope of the invention. For example, any suitable means of attaching connector 12 to the laser source may be used in place of the bayonet mount discussed above. Also, surface 30 of the preferred embodiment and surface 164 of the alternative embodiment may have a complex slope instead of the straight conical shape described above. In addition, the invention may be used with optical fibers other than waveguides. Other changes and modifications will be apparent to those skilled in the art.

What is claimed is:

1. An optical transmission device comprising:
   a body having an optical radiation inlet and an optical radiation outlet;
   a tapered surface disposed in the body between the inlet and the outlet, the tapered surface having an inlet aperture and an outlet aperture;
   means for attaching an optical transmission means to the body, the means for attaching being disposed in the body between the outlet aperture of the tapered surface and the body outlet.

2. The optical transmission device of claim 1 wherein the optical transmission means is an optical fiber.

3. The optical transmission device of claim 1 wherein the optical transmission means is an optical waveguide.

4. The optical transmission device of claim 3 wherein the optical waveguide is hollow.

5. The optical transmission device of claim 4 wherein the means for attaching is a bore formed in the body, the inner diameter of the hollow waveguide having a diameter smaller than the outlet aperture of the tapered surface.

6. The optical transmission device of claim 1 wherein the tapered surface has a conical shape.

7. The optical transmission device of claim 1 further comprising reflectance enhancement means on the tapered surface.

8. The optical transmission device of claim 1 further comprising means for attaching the body to an optical radiation source.

9. The optical transmission device of claim 1 further comprising means for attaching an accessory to the body.

10. The optical transmission device of claim 1 wherein the optical transmission means is a waveguide comprising a hollow core surrounded by a jacket, the means for attaching the optical transmission means to the body comprising first and second bores formed in the body, the first bore having a diameter substantially equal to the outer diameter of the core, the second bore having a diameter substantially equal to the diameter of the jacket.

11. The optical transmission device of claim 10 wherein the diameter of the outlet aperture of the tapered surface is smaller than the diameter of the first bore.

12. The optical transmission device of claim 1 wherein the body is formed in one piece.

13. An optical transmission device comprising:
   a body having an optical radiation inlet and an optical radiation outlet;
   a tapered surface disposed in the body between the inlet and the outlet, the tapered surface having an inlet aperture and an outlet aperture;
   means for attaching a hollow optical transmission means to the body, the means for attaching being disposed in the body between the outlet aperture of the tapered surface and the body outlet, the diameter of the hollow optical transmission means being smaller than the diameter of the outlet aperture of the tapered surface.

14. The optical transmission device of claim 13 wherein the tapered surface has a conical shape.

15. The optical transmission device of claim 14 wherein the body is formed as one piece.

16. An optical transmission device comprising:
   a body having an optical radiation inlet and an optical radiation outlet;
   a tapered surface disposed in the body between the inlet and the outlet, the tapered surface having an inlet aperture and an outlet aperture;

means for attaching an optical transmission means to the body, the means for attaching being disposed in the body between the outlet aperture of the tapered surface and the body outlet, the means for attaching comprising a bore formed in the body, the diameter of the bore being larger than the diameter of the outlet aperture of the tapered surface.

17. The optical transmission device of claim 16 wherein the tapered surface has a conical shape.

18. The optical transmission device of claim 17 wherein the body is formed as one piece.

19. The optical transmission device of claim 18 wherein the optical transmission means is a hollow waveguide, the inner diameter of the hollow waveguide being smaller than the diameter of the outlet aperture of the tapered surface.

20. The optical transmission device of claim 19 further comprising reflectance enhancement means on the tapered surface.

* * * * *